(12) United States Patent  
Fishman

(10) Patent No.: US 11,728,064 B2
(45) Date of Patent: Aug. 15, 2023

(54) COUPLED RING ANODE WITH SCANNING ELECTRON BEAM BREMSSTRAHLUNG PHOTON FLUX INTENSIFIER APPARATUS

(71) Applicant: Empyrean Medical Systems, Inc., Boca Raton, FL (US)

(72) Inventor: Kalman Fishman, Boca Raton, FL (US)

(73) Assignee: EMPYREAN MEDICAL SYSTEMS, INC, Boca Raton, FL (US)

( * ) Notice: Subject to any disclaimer, the term of this patent is extended or adjusted under 35 U.S.C. 154(b) by 273 days.

(21) Appl. No.: 17/218,986

(22) Filed: Mar. 31, 2021

(65) Prior Publication Data

US 2021/0299477 A1  Sep. 30, 2021

Related U.S. Application Data

(60) Provisional application No. 63/002,809, filed on Mar. 31, 2020.

(51) Int. Cl.
| | |
|---|---|
| *A61N 5/10* | (2006.01) |
| *G21K 1/06* | (2006.01) |
| *H01J 5/30* | (2006.01) |
| *H01J 35/14* | (2006.01) |
| *A61B 5/00* | (2006.01) |

(Continued)

(52) U.S. Cl.
CPC ............. *G21K 1/067* (2013.01); *A61B 6/025* (2013.01); *A61N 5/1042* (2013.01); *A61N 5/1043* (2013.01); *A61N 5/1071* (2013.01); *G21K 1/062* (2013.01); *H01J 35/153* (2019.05); *H01J 35/30* (2013.01); *A61N 5/103* (2013.01); *A61N 5/1031* (2013.01); *A61N 2005/1054* (2013.01)

(58) Field of Classification Search
CPC ...... A61B 6/025; A61N 5/103; A61N 5/1031; A61N 5/1042; A61N 5/1043; A61N 5/1071; A61N 2005/1054; G21K 1/062; G21K 1/067; H01J 35/153; H01J 35/30
See application file for complete search history.

(56) References Cited

U.S. PATENT DOCUMENTS

| 9,008,271 B2 | 4/2015 | Burshtein et al. |
| 9,586,061 B2 | 3/2017 | Burshtein et al. |

(Continued)

FOREIGN PATENT DOCUMENTS

| CA | 2973781 A1 | 9/2012 |
| WO | 2004042769 A1 | 5/2004 |

OTHER PUBLICATIONS

International Search Report mailed in PCT/US21/25145 dated Jul. 19, 2021.

*Primary Examiner* — Mark R Gaworecki
(74) *Attorney, Agent, or Firm* — Fox Rothschild LLP

(57) ABSTRACT

A radiation therapy device includes an electron beam source (EBS) for generating an electron beam and a steering device for directing the electron beam. A target is disposed a predetermined distance from the EBS and is positioned to intercept the electron beam. The target element generates x-ray photons upon the impact of electrons with the target. A focusing lens is coupled to and spaced from the target by no more than 10 mm, and is positioned to receive x-ray photons generated by the target. The focusing lens focuses the x-ray photons to a focal point. The radiation therapy device can also include targets configured to generate x-ray beams for tomosynthesis. A method for performing radiation therapy is also disclosed.

34 Claims, 16 Drawing Sheets

(51) Int. Cl.
    *H01J 35/30*     (2006.01)
    *A61B 6/02*     (2006.01)

(56) References Cited

U.S. PATENT DOCUMENTS

| | | |
|---|---|---|
| 9,953,735 B2 | 4/2018 | Bar-David et al. |
| 10,099,068 B2 | 10/2018 | Burshtein et al. |
| 10,265,510 B2 | 4/2019 | Harel et al. |
| 10,607,802 B2 | 3/2020 | Fishman et al. |
| 2005/0105690 A1 | 5/2005 | Pau et al. |
| 2017/0047191 A1 | 2/2017 | Yun et al. |
| 2017/0318652 A1 | 11/2017 | Meiler et al. |
| 2018/0033513 A1 | 2/2018 | Bar-David et al. |
| 2018/0353775 A1 | 12/2018 | Bar-David et al. |
| 2019/0175953 A1 | 6/2019 | Bar-David et al. |
| 2020/0058462 A1 | 2/2020 | Suzuki |

COUPLED RING ANODE WITH SCANNING ELECTRON BEAM BREMSSTRAHLUNG PHOTON FLUX INTENSIFIER APPARATUS

CROSS REFERENCE TO RELATED APPLICATIONS

This application claims priority to U.S. Provisional Patent Application No. 63/002,809 filed on Mar. 31, 2020 entitled "COUPLED RING ANODE WITH SCANNING ELECTRON BEAM BREMSSTRAHLUNG PHOTON FLUX INTENSIFIER APPARATUS", the entire disclosure of which is incorporated herein by reference.

FIELD OF THE INVENTION

The present invention relates generally to radiation therapy, and more particularly to external beam radiation therapy systems and methods.

BACKGROUND OF THE INVENTION

External beam radiation therapy involves the creation of a beam of x-ray photons, and sometimes a beam comprised of electrons or protons, and directing this beam to a treatment area of a patient, for example a tumor. X-ray photon radiation is commonly produced by creating and steering a beam of electrons at a target. The target material is selected to produce Bremsstrahlung interactions, wherein the sudden deceleration of the electrons at the target generates x-ray photons. The x-ray photons so generated are dispersed, and must be focused and steered to the treatment area. Many different x-ray focusing devices are known, including for example the Rowland lens, the spectral x-ray focusing lens, and the rolled x-ray prism lens. Such x-ray radiation therapy devices can experience very significant x-ray attenuation from the target to the treatment area. The attenuation of the x-ray photon energy in such devices can be as high as 50% or more.

SUMMARY OF THE INVENTION

A radiation therapy device includes an electron beam source (EBS) for generating an electron beam, a steering device for directing the electron beam, and a target disposed a predetermined distance from the EBS and positioned to intercept the electron beam, the target element generating x-ray photons upon the impact of electrons with the target. A focusing lens is coupled to and spaced from the target by no more than 10 mm, and positioned to receive x-ray photons generated by the target. The focusing lens focuses the x-ray photons to a focal point.

The electron beam source and the steering device can generate a scanning electron beam. The steering device can include a deflecting electromagnet for scanning the electron beam. The focusing lens has an inlet geometry and the target can be shaped to match the inlet geometry of the focusing lens. The attenuation of the x-ray photons from the target to the lens can be less than 15%.

The target can include a material which produces Bremsstrahlung x-rays when impacted by electrons generated by the electron beam source. The target can include at least one selected from the group consisting of molybdenum, gold, tungsten, rhodium, and brass. The focusing lens can comprise of at least one selected from the group consisting of mirrors, crystals, and polyimide film over a substrate.

The radiation therapy device can include a focusing device for focusing electrons in a pattern. The pattern can be at least one selected from the group consisting of a pencil beam, a cone beam, and an O-shaped beam. The radiation therapy device can further include a cooling circuit for facilitating the transfer of thermal energy away from the target.

The radiation therapy device can include an electron beam source control system that is configured to selectively control the location where the electron beam intersects the target. The EBS control system can be configured to selectively control an x-ray dose by selectively varying at least one of an EBS voltage and an electron beam dwell time which are applied when the electron beam intersects the target.

The radiation therapy device can further include a vacuum chamber disposed between the electron beam source and the target. The electron beam source can be configured to cause the electron beam to travel through an enclosed elongated length of the vacuum chamber maintained at a vacuum pressure.

The target is provided on a substrate layer. The substrate layer can include at least one material selected from the group consisting of diamond, beryllium, aluminum, sapphire, and ceramic.

The focusing lens can be at least one selected from the group consisting of a Rowland lens, a spectral x-ray focusing lens, and a rolled x-ray prism lens. The focusing lens can include concentric focusing lens elements. The concentric focusing lens elements can decrease in diameter in direction extending away from the EBS.

The radiation therapy device can further include a target-aligning septa comprising a high Z material. The high Z material can be at least one selected from the group consisting of stainless steel, molybdenum (Mo), tungsten (W), and tantalum (Ta). The radiation therapy device can include lens-coupled septa comprising a high-Z material, where the lens aligning septa is positioned between the target and the focusing lens.

The radiation therapy device can further include a tomography target for generating tomography multiplane cone beam x-ray photon beams. The radiation therapy device can also include an x-ray photon detector for detecting the tomography multiplane cone beam x-ray photon beams. The detector can be movable from a first registered position to a second registered position. The tomography target can be positioned in the center axis of concentric focusing lens elements. The radiation therapy device can have a plurality of tomography targets mounted on a concave substrate. The concave substrate can be parabolic.

The radiation therapy device can be mounted on a positioning device. The positioning device comprises at least one selected from the group consisting of a rotating powered gantry, a robotic gantry, and a manually controlled arm.

A method for conducting radiation therapy can include the step of providing an electron beam source (EBS) for generating an electron beam, a steering device for directing the electron beam, and a target disposed a predetermined distance from the EBS and positioned to intercept the electron beam. The target generates x-ray photons upon the impact of electrons with the target. A focusing lens is coupled to and spaced from the target by no more than 10 mm and positioned to receive x-ray photons generated by the target.

An electron beam is generated with the EBS and using the steering device to direct the electron beam to the target. The target will generate x-ray photons that will impact the focusing lens. The x-ray photons are focused with the focusing lens to a focal point.

The focusing lens has an inlet geometry and the target is shaped to match the inlet geometry of the focusing lens. The focusing of the x-ray photons can be performed by at least one selected from the group consisting of a Rowland lens, a spectral x-ray focusing lens, and a rolled x-ray prism lens.

The method can further include the steps of providing a tomography target, directing the electron beam at the tomography target, and generating tomography multiplane cone beam x-ray photon beams by the impact of the electron beam with the tomography target. The method can further include the step of providing an x-ray photon detector, and using the x-ray photon detector for detecting the tomography multiplane cone beam x-ray photon beams. The method can also include the step of registering a first position of the x-ray detector, and moving the x-ray detector from the first registered position to a second registered position.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

Figure 1:
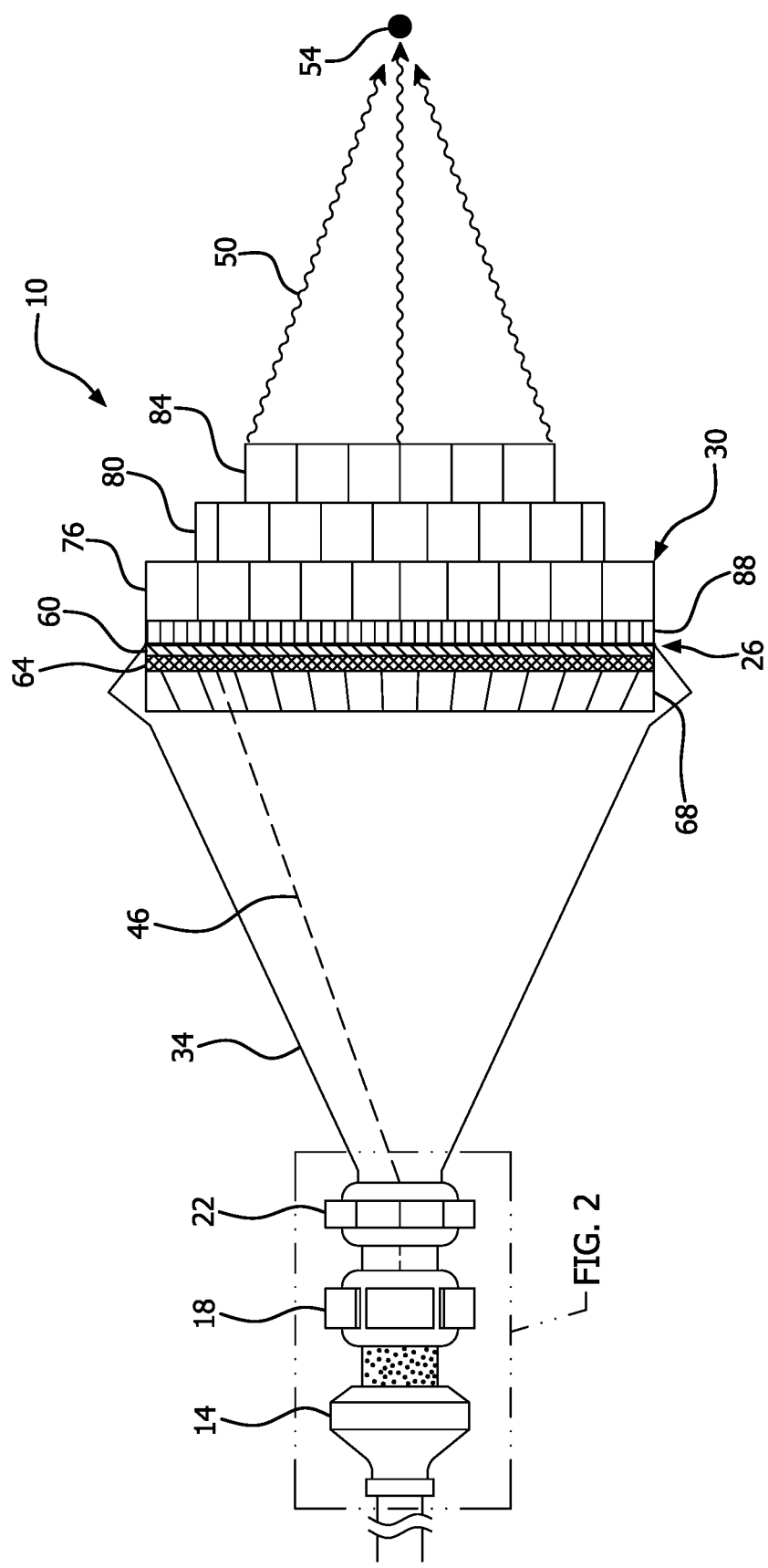
FIG. 1 is a schematic diagram of a radiation therapy device according to the invention.

A radiation therapy device includes an electron beam source assembly which can include an electron beam source (EBS) for generating an electron beam and a steering device for directing the electron beam. A target is disposed a predetermined distance from the EBS and is positioned to intercept the electron beam. The target element generates x-ray photons upon the impact of electrons with the target. A focusing lens is coupled to and spaced from the target by no more than 10 mm, and is configured and positioned to receive x-ray photons generated by the target. The focusing lens focuses the x-ray photons to a focal point.

The electron beam assembly, target and focusing lens can be mounted in a treatment head, which can in turn be mounted on a suitable positioning device for positioning and aiming the x-ray beam to a desired focal point. For example, the treatment head can be mounted on a robotic arm, or on a gantry.

The focusing lens has an inlet geometry and the target can be shaped to match the inlet geometry of the focusing lens. For example, the focusing lens can have a circular inlet geometry, and the target can be correspondingly circular. The focusing lens can have a semicircular geometry, and the target can be correspondingly semicircular. Other focusing lens inlet geometries are possible, and the target can be configured to that geometry. The target contour can match and follow the contour of the focusing lens inlet.

The electron beam source assembly can include components for focusing and steering the dispersed electrons generated by the EBS. These can include a beam focusing device for confining the dispersed electrons into a desired pattern, and a steering device.

The EBS is commonly a cathode connected to a high voltage supply disposed in a vacuum chamber and controlled by the central control unit circuitry. Many different electron beam sources are known and can be used in the invention.

The steering device can be any suitable steering device. The steering device comprises a deflecting electromagnet for scanning the electron beam. Other steering devices are possible. The steering device can be utilized with a pencil beam to scan that beam across a target in selected locations at selected times and frequencies. In the case of a circular target, for example, the scanning electron beam can be steered in a circular pattern.

The electron beam source assembly can include a beam focusing device for focusing electrons into a desired pattern and focal spot. The pattern can vary. The pattern for example can be at least one selected from the group consisting of a pencil beam of a certain diameter, a solid cone beam, and a hollow O-shaped beam for striking a circular target. Other patterns are possible. The beam focusing device as is known generates variable magnetic fields which are used to influence the electrons into the desired pattern.

The target is coupled to the focusing lens. The term 'coupled' as used herein means that the target and focusing lens are in contact, or in very close proximity and connected together. The separation of the target and the inlet of the focusing lens can be between 0 (directly in contact) and 10 mm. The separation of the target and the inlet of the focusing lens can be 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 and 10 mm, or within a range of any high value and low value selected from these values.

The connection between the target and the focusing lens can be mechanical, chemical, or otherwise, and can be direct or indirect, but can be direct or indirect. In a direct connection the target is directly in contact with the inlet portion of the focusing lens. The target can be secured directly to the focusing lens. In an indirect connection, the target and the focusing lens are separated by space or by other structure such as an x-ray aligning septa, connecting structure, or the x-ray window, which is also the seal of the vacuum chamber. The target and focusing lens can be physically connected through adjacent connecting structure such as a supporting framework, the housing of a treatment head, or other suitable structure. The connection between the target and the focusing lens should be such that they are not separated by more than 10 mm. Portions of the focusing lens away from the focusing lens inlet can and will often be separated from the target by more than 10 mm, however, the distance that the x-ray photons travel from the target to the inlet of the focusing lens should be 10 mm or less. X-ray photons generated at the target will thereby immediately reach the inlet of the focusing lens, with minimal to no attenuation.

The attenuation of the x-ray photons flux, both from an x-ray photon per unit area and the energy of the x-ray photons, is reduced significantly by the invention. The attenuation of the x-ray photons from the target to the lens is less than 15%. The attenuation of the x-ray photons to the lens can be 0, 0.01, 0.02, 0.03, 0.04, 0.05, 0.06, 0.07, 0.08, 0.09, 0.1, 0.2, 0.3, 0.4, 0.5, 0.5, 0.7, 0.8, 0.9, 1, 2, 3, 4, 5, 6, 7, 8, 9, 10, 11, 12, 13, 14, and 15%, and can be within a range of any high value and low value selected from these values.

The target material is selected to produce Bremsstrahlung interactions which generate x-ray photons when impacted by electrons generated by the electron beam source. The target material can include at least one selected from the group consisting of molybdenum, gold, tungsten, rhodium, and brass. Other target materials are possible.

Various constructions of the target are possible. The target material can be provided on a substrate layer. The substrate layer should support the target material, should not be reactive with the target material, and should be transmissive of the electron-beam with minimal attenuation of the energy of the electron beam. The substrate layer comprises at least one material selected from the group consisting of diamond, beryllium, aluminum, sapphire, and ceramic. Other substrate materials are possible.

There are many different focusing lens designs that would be suitable for the invention. The focusing lens can, for example, be a Rowland lens, a spectral x-ray focusing lens, or a rolled x-ray prism lens. One example of an improved Rowland type lens is shown in Bar-David et al US 2018/0033513, the disclosure of which is incorporated by reference. The materials and focusing lens elements can vary. For example, the focusing lens comprises at least one selected from the group consisting of mirrors, crystals, and polyimide film over a substrate. Other focusing lens constructions and construction materials can be utilized with the invention. The focusing lens in one design can include concentric lens elements. The concentric lens elements can decrease in diameter in direction extending away from the EBS.

The radiation therapy device can include target-aligning septa. The target-aligning septa can comprise a high Z material. The target aligning septa pass only the portions of the electron beam that are aligned with the target, and absorb electrons that are not aligned with the target. The high Z material can be, for example, stainless steel, molybdenum (Mo), tungsten (W), and/or tantalum (Ta). The target-aligning septa reduces the amount of scatter and cross-interaction of electrons with the target, thus optimizing the x-ray photons produced by the Bremsstrahlung interaction between the atoms of the target and the EBS electrons.

A trajectory alignment septa for x-rays generated at the target can also be utilized between the target and the focusing lens. This lens-coupled septa prevents scattered x-ray photons from illuminating non-targeted areas or sections of the inlet portion of the focusing lens. The lens-coupled septa can also be formed from a high-Z material, such as used for the target aligning septa, or can comprise different materials. The lens aligning septa is positioned between the target and the inlet portion of the focusing lens, and passes x-ray photons that are aligned with the inlet of the focusing lens, and blocks and absorbs x-ray photons that are not aligned with the inlet of the focusing lens.

The target can become hot due to the bombardment by the electron beam. Cooling the target can be accomplished by suitable heat transfer methods and devices. A cooling circuit for facilitating the transfer of thermal energy away from the target by means of a flowing cooling fluid can be utilized. Other heat transfer methods and devices are possible.

Control systems and devices can be provided for the radiation therapy device. An electron beam source assembly control system can be configured to selectively control the location where the electron beam intersects the target. The control can be a suitable processor and control circuitry, including the control firmware and software, which control the components of the radiation therapy device, such as the electron beam source, the focusing device, and the steering device. Sensors can provide input to the processor such as temperature sensors, radiation sensors, fluid flow sensors, position sensors, tomosynthesis x-ray detectors, and other detectors and control devices. The electron beam source control system can be further configured to selectively control an x-ray dose by selectively varying at least one of an electron beam source voltage, electron beam focal spot size and shape, and an electron beam dwell time on the target, which are applied when the electron beam intersects the target.

The electron beam source usually operates in a vacuum to avoid the interference and attenuation of the electron beam due to interaction with air. A vacuum chamber can be disposed between the electron beam source assembly and the target. The electron beam source assembly can be configured to cause the electron beam to travel through an enclosed elongated length of the vacuum chamber maintained at a vacuum pressure. An ion pump can be connected to the vacuum chamber in order to eliminate gases generated at the target during a Bremsstrahlung interaction between the electron beam and the target atoms.

The radiation therapy device of the invention can also be configured to perform tomography. A tomography target can be provided for generating tomography multiplane x-ray cone beam. An x-ray photon detector can be provided for detecting the tomography multiplane x-ray cone beam. The treatment head and the detector can be relatively movable from a first known position to a second known position. The detector provides detector signals to a suitable processor to generate tomographic filter back projected images. These images can then be used as input image guiding data for the treatment planning software to generate a treatment plan for the radiation therapy, including control signals for the electron beam source assembly, as well as the positioning of these components when contained within a mobile treatment head.

The tomography target can be located in different positions relative to the treatment target that is coupled to the focusing lens inlet. In one embodiment where the focusing lens is concentric, the tomography target can be positioned in and around the center axis of concentric focusing lens elements. A plurality of tomography targets can be provided. The tomography targets can be mounted on a suitable substrate, and in one embodiment can be mounted on a concave substrate. The concave substrate can be parabolic. The substrate can be made of the same materials as used for the treatment target substrate.

The radiation therapy device components of the invention can be mounted within a treatment head housing and mounted on a positioning device. The positioning device can, for example, be a powered rotating gantry, a robotic gantry, or a manual mechanical arm. This allows controlled and registered positioning of the radiation therapy device, and particularly its focal point. The positioning device can be mobile, for example on wheels which can be electric motor powered. Other positioning devices and mobile positioning devices are possible.

A method for conducting radiation therapy includes the step of providing an electron beam source assembly, including and electron beam source (EBS) for generating an electron beam, possibly a beam focusing device, and a steering device for directing the electron beam. A target is disposed at a predetermined distance from the electron beam source assembly and positioned to intercept the electron beam. The target generates x-ray photons upon the impact of electrons with the target. A focusing lens is coupled to and spaced from the target by no more than 10 mm and an inlet portion of the focusing lens is configured and positioned to receive x-ray photons generated by the target. The electron beam is generated by the electron beam source assembly and the steering device is used to direct the electron beam to the target. The target will generate x-ray photons that will enter the focusing lens inlets. The x-ray photons are focused by the focusing lens to a focal point.

Figure 2:
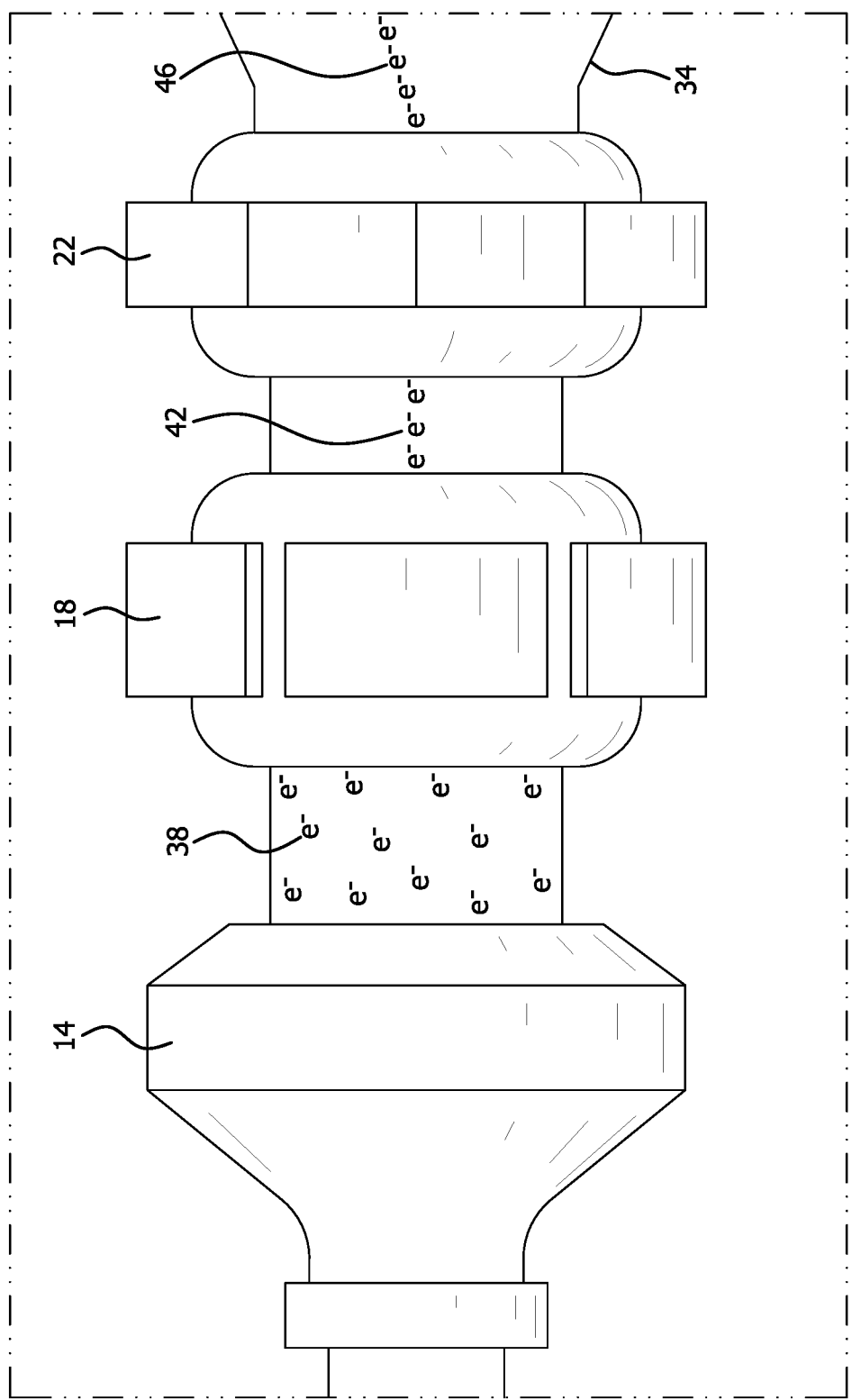
FIG. 2 is an expanded view of area FIG. 2 in FIG. 1.

There is shown in FIGS. 1-4 a radiation therapy device 10 according to the invention. The radiation therapy device 10 includes an electron beam source assembly (FIG. 2) which can include electron beam source 14, a beam focusing device 18, and a beam steering device 22. Many different devices exist for generating, shaping and steering electron beams and many such devices could be utilized and are within the scope of the invention. For example, one or more of an electron beam source, beam focusing device, and steering device can be incorporated into a single device or in more devices. As shown in FIG. 2, the electron beam source 14 generates a plurality of electrons 38. The electron beam generated by the electron beam source 14 is sometimes unfocused and lacks a coordinated beam geometry. The beam focusing device 18 incorporates circuitry such as but not limited to electromagnets for shaping and focusing the electron beam as desired. As shown in FIG. 2, in one aspect the desired beam can be a pencil beam of electrons 42, however, other desired shapes such as O-shapes, cone shapes, and shapes specifically designed for the target and/or focusing lens inlet geometry that are used can be created.

The electron beam created by the electron beam source assembly will in most cases require some element of steering in order that the electron-beam is properly directed at the target. The electron beam may be actively scanned across the target. In the case of a circular target this scanning can also be in a circular motion. The steering can be accomplished by many different beam steering devices shown generally as beam steering device 22. The beam steering device 22 in one embodiment is a series of coils generating a controllable electromagnetic field to steer the electron beam in any desired direction towards the target. The steered electron beam 46 then passes through a vacuum chamber 34 towards the target.

Figure 3:
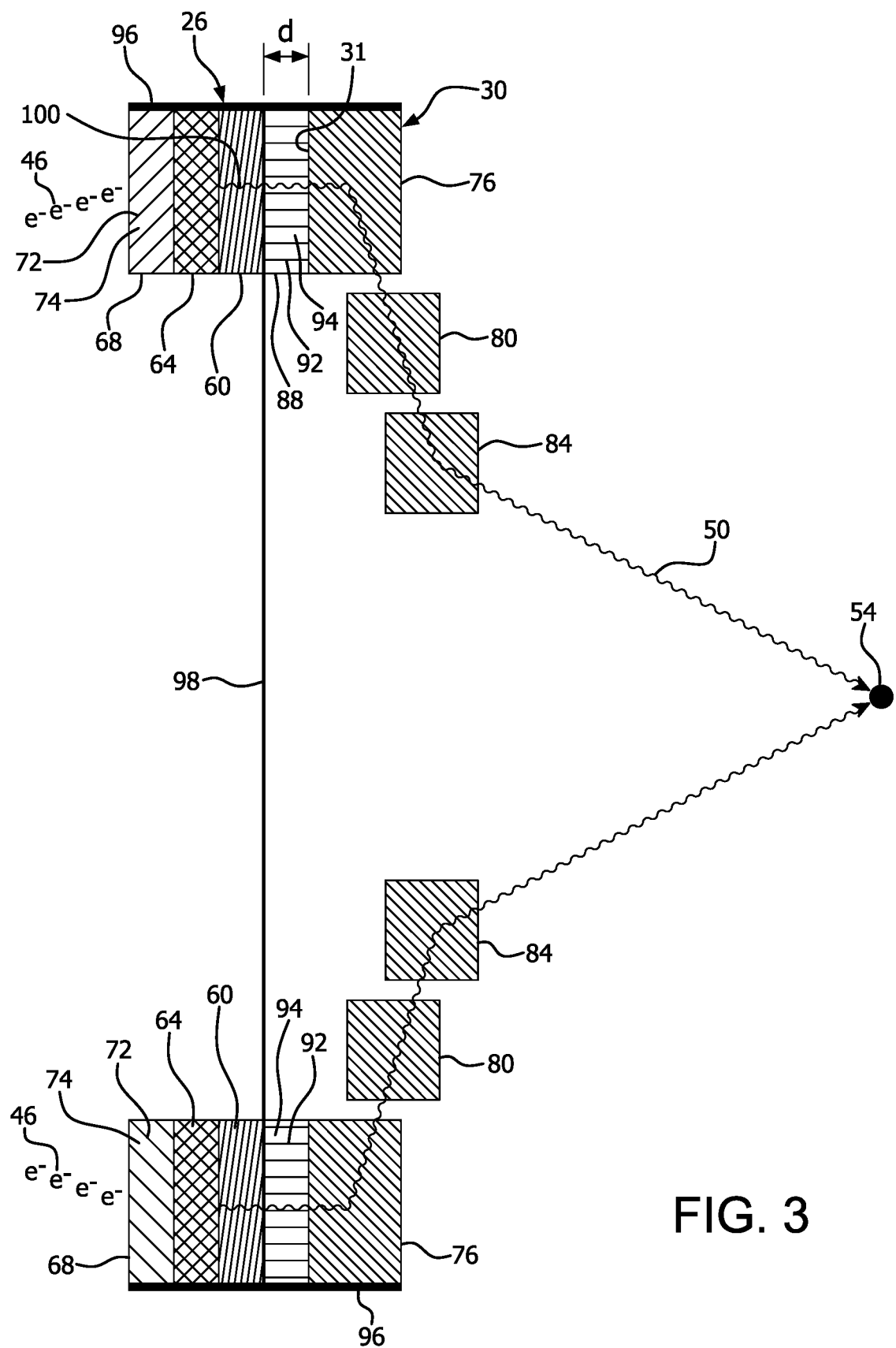
FIG. 3 is a schematic cross-section of a target and x-ray focusing lens.

The target 26 is impacted by the steered electron beam 46 to generate x-ray photons, as shown in FIG. 3. The x-ray photons are focused by the focusing lens 30 and emerge as focused x-ray photons 50 that converge on the desired treatment focal point 54. The target 26 has a geometry that can be configured to match the geometry of the inlet portion 31 of the focusing lens 30. In the embodiment that is shown, the inlet geometry is essentially circular, however, it should be appreciated that many different focusing lens inlet geometries are possible. The target should be coupled to the focusing lens such that x-rays emanating from the target immediately enter the focusing lens through the inlet portion of the lens, or travel no more than 10 mm before entering the focusing lens inlet. The inlet portion of the focusing lens is the receiving surface of the focusing lens, closest to the target. The target 26 can be a composite consisting of a target material 60 on a suitable target substrate layer or support 64. The target substrate layer 64 may not be necessary in all cases. Also, the target 26 can include structure for excluding electrons which are not properly aligned with the target 60. Such structure can be a target-aligning septa 68, which includes a plurality of vanes 72 which are made of a high Z material. Only electrons of the steered electron beam 46 which are properly aligned with the target 60 will pass through space 74 between the vanes 72. The steering device 22 can be used to steer the electron beam 46 to particular portions of the target 26 in order to properly cover all necessary parts of the target and, subsequently, follow the geometry of the inlet 31 of the focusing lens 30.

The focusing lens 30 is coupled to the target 26 and separated by a distance 'd' that is no more than 10 mm. The particular focusing lens 30 that is shown is comprised of concentric rings such as outermost ring 76, middle ring 80, and innermost ring 84. Different focusing lens designs and constructions are possible. The space 'd' between the target 60 and the outermost focusing lens ring 76 can be open, however in the embodiment shown includes a lens-coupled septa 88. The lines-coupled septa 88 includes a plurality of vanes 92 creating spaces 94 there between for the passage of x-ray photons. An end wall 98 of the vacuum chamber 34 seals the space between the electron beam source assembly and the focusing lens 30 so as not to attenuate the electron beam. Schematic connecting structure 96 mechanically connects the target 26 to the focusing lens 30. This connecting structure can be a framework, a portion of a treatment head housing, or other structure both singular and plural, holds the components in proper position. In some cases the target can be directly connected to the inlet of the focusing lens.

The steered electron beam 46 encounters the target 60 and generates x-ray photons 100. These x-ray photons pass through the lens-coupled septa 88 and are focused by a cascade through the inlet of the outermost focusing lens ring 76, middle focusing lens ring 80, and innermost focusing lens ring 84, and then travels from the focusing lens 30 as the x-ray photon beam 50 directed at the treatment focal point 54.

Figure 4:
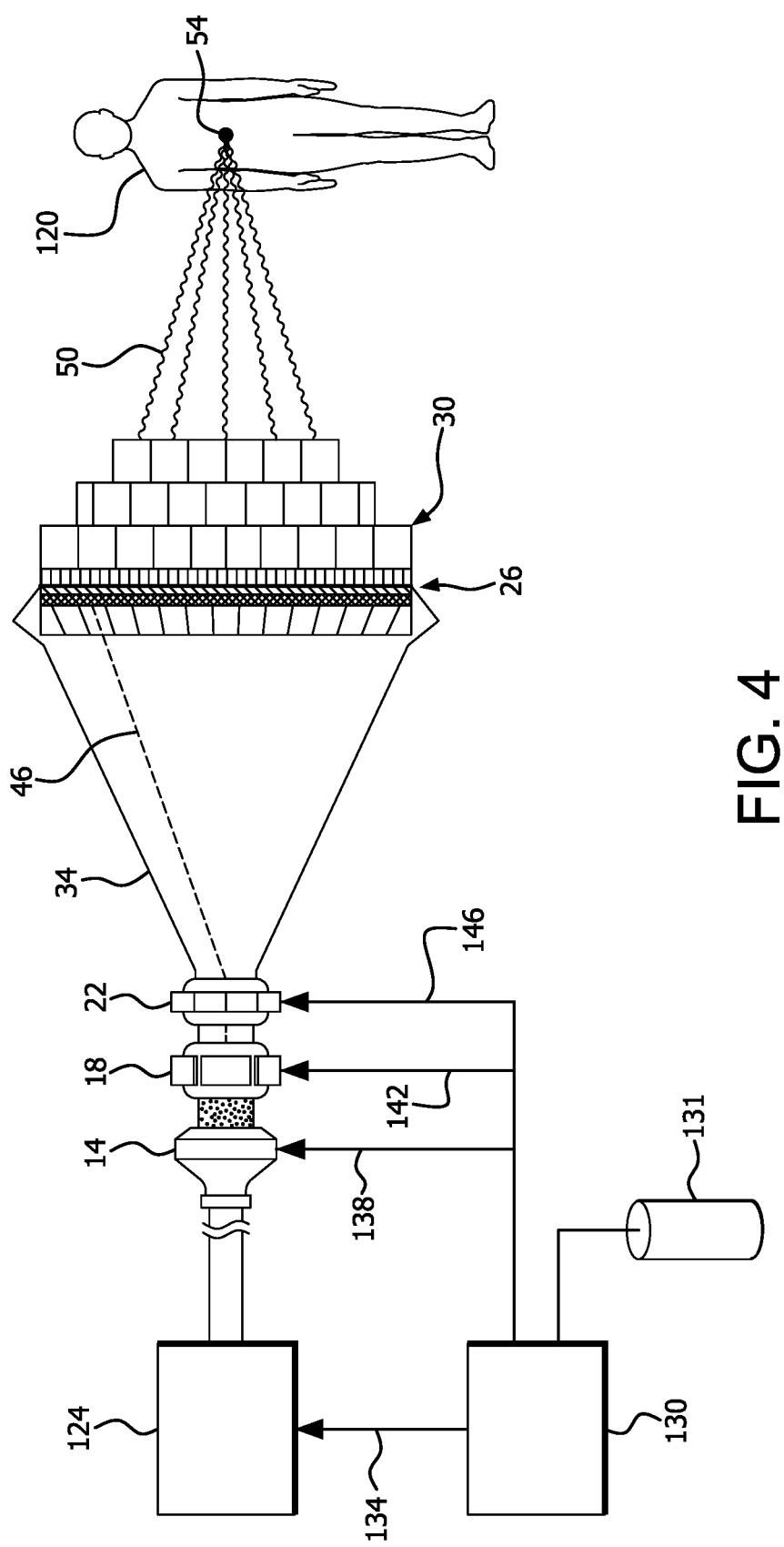
FIG. 4 is a schematic diagram of a radiation therapy device according to the invention as used on a patient.

The schematic treatment of the patient 120 is shown in FIG. 4. The treatment focal point 54 is representative of the location of the treatment, for example a tumor. A processor 130 controls the operation of the radiation therapy device and can be connected to a data storage repository 131. A high voltage generator 124 connects high voltage to the electron beam source 14 and is controlled by the processor 130 through a control connection 134 which can be wired or wireless. The processor 130 can control the electron beam source 14 through a control connection 138. The processor 130 can control the beam focusing device 18 through a suitable control connection 142. The processor 130 can control the beam steering device 22 through a suitable control connection 146. Other control configurations are possible. The processor 130 stores the treatment plan for the patient 120 and performs the treatment operation for the patient 120 through control of system components.

Figure 5:
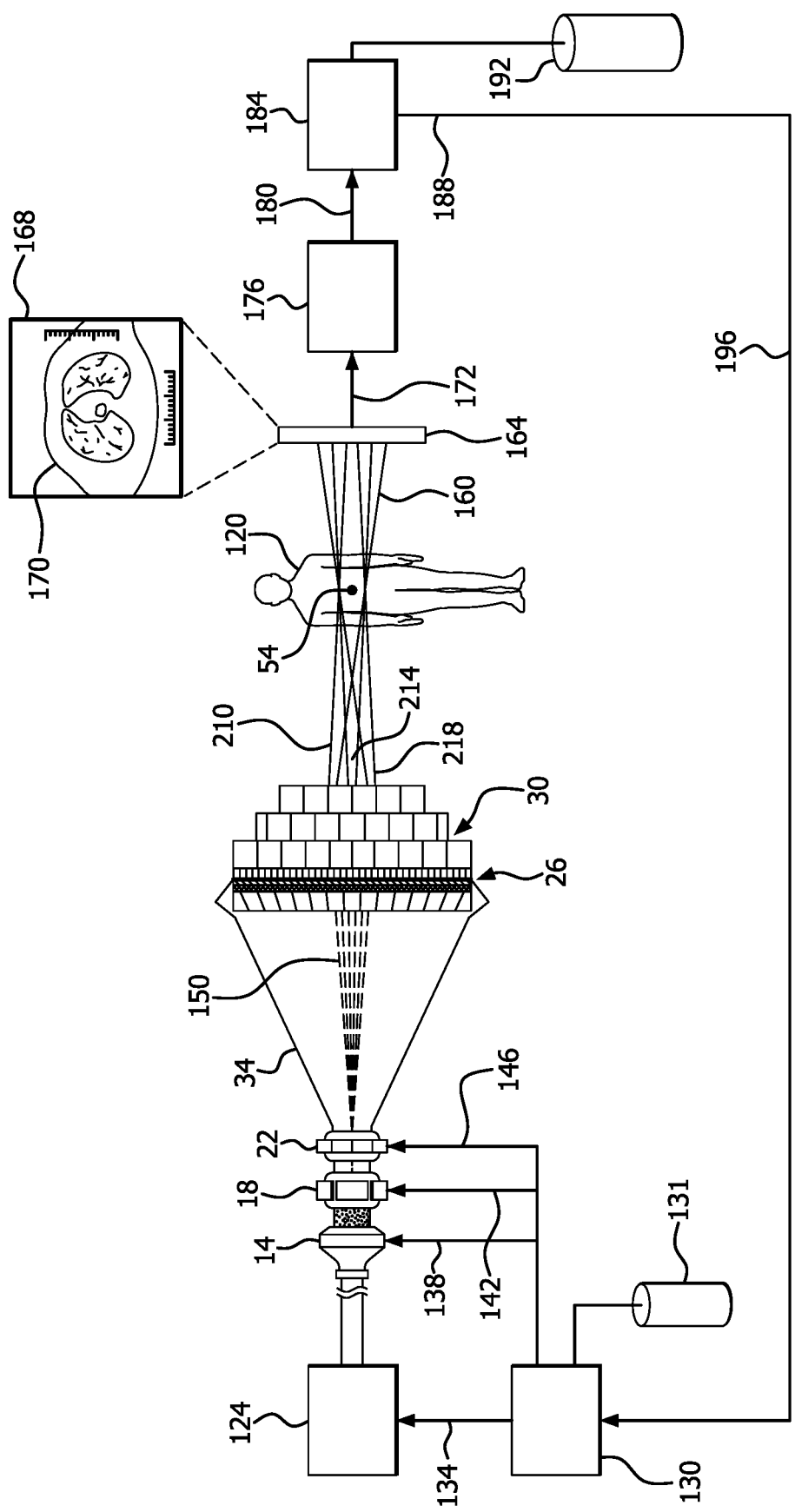
FIG. 5 is a schematic diagram of a radiation therapy device according to the invention as used on a patient in a tomosynthesis mode of operation.
Figure 6:
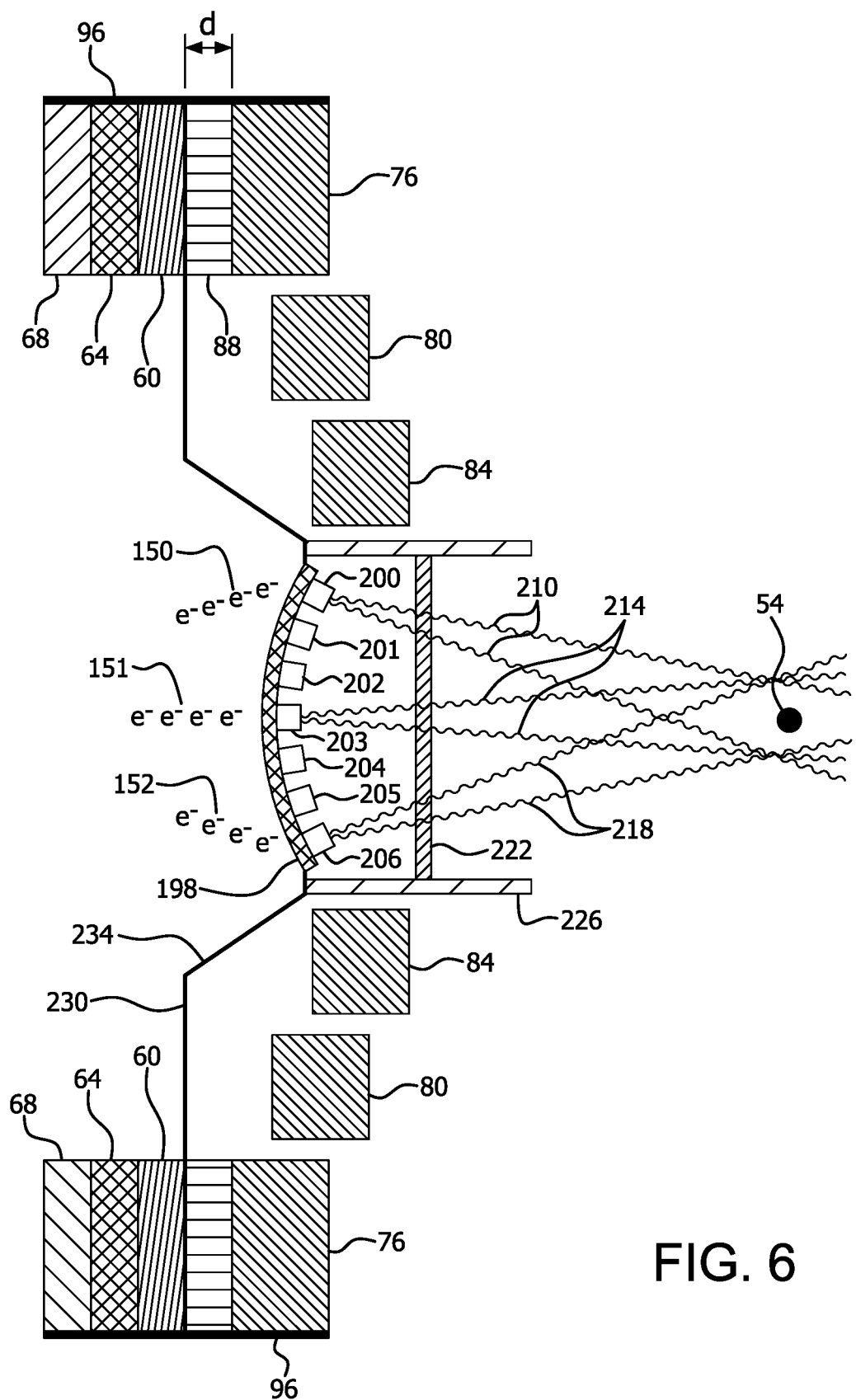
FIG. 6 is a schematic cross-section of a target and focusing lens in a tomosynthesis mode of operation.

The radiation therapy device of the invention can be constructed so as to also be capable of generating anatomical x-ray images for the purpose of image-guided treatment planning and diagnostics. The imaging types that can be generated by the device include cone beam computed tomography, tomosynthesis, planar x-ray, and other x-ray imaging methods. Such an embodiment is shown in FIGS. 5-6, where like numbers refer to like elements. In such an embodiment, the electron beam source assembly generates a steered electron beam 150 for tomosynthesis. In the embodiment shown in FIGS. 5-6, tomosynthesis targets are positioned within the center of the concentric outermost focusing lens ring 76, middle focusing lens ring 80, and innermost focusing lens ring 84 of the focusing lens 30. Other positions and configurations for the tomosynthesis targets are possible. As shown particularly in FIG. 6, a substrate layer 198 which can be constructed similarly to the substrate layer used for the target 26 is provided with a number of tomosynthesis targets 200-206. More or fewer tomosynthesis targets are possible. The substrate layer 198 can have differing dimensions and shapes. In one embodiment, the substrate layer 198 is concave, and in a further embodiment can be parabolic, or planar. End wall 230 can be provided to seal the vacuum chamber and a connecting 234 can be provided to connect with and seal the tomosynthesis substrate layer 198. A beam hardening filter 222 can be provided in front of the tomosynthesis cone beams to optimize the beam quality for the purpose of conducting tomosynthesis imaging. The filter 222 can be made of Aluminum (Al), Cupper (Cu), and other materials. The filter 222 and substrate layer 198 with targets 200-206 can be mounted with a supporting structure 226.

The steered tomosynthesis electron beam 150 is transmitted through the substrate layer 198 and strikes one or more of the tomosynthesis targets 200-206. As the tomosynthesis targets 200-206 are differently oriented due to their position on the curved substrate layer 198, differently directed cone beams are produced. For example, when the steered tomosynthesis electron beam 150 strikes the tomosynthesis target 200, a cone beam 210 is produced. Similarly, when the steered tomosynthesis electron beam 151 strikes the target 203, a differently directed cone beam 214 is produced. When the steered tomosynthesis beam 152 strikes the target 206, a cone beam 218 is produced. The cone beams 210, 214 and 218 intersect at the intended imaging and treatment areas indicated by the focal point 54 of the patient 120. The differently directed cone beams emerging as x-ray photon signals 160 which strike a detector 164. A three-dimensional image is generated by suitable x-ray image processing software as indicated by the x-ray image 168 of a portion 170 of the patient 120. This can be accomplished by a signal 172 sent to a data acquisition module 176, which through a suitable connection 180 then passes information to radiation treatment planning software 184 and through a connection 188 to suitable data storage 192. The treatment planning software 184 then passes the treatment plan to the processor 130 through a connection 196. The processor 130 utilizes the treatment plan to control the electron beam source assembly to provide appropriate treatment to the patient 120. The data storage 192 is utilized to back up the treatment plan generated by the treatment planning software 184. It will be appreciated that certain of these modules can be modified or combined.

Figure 7:
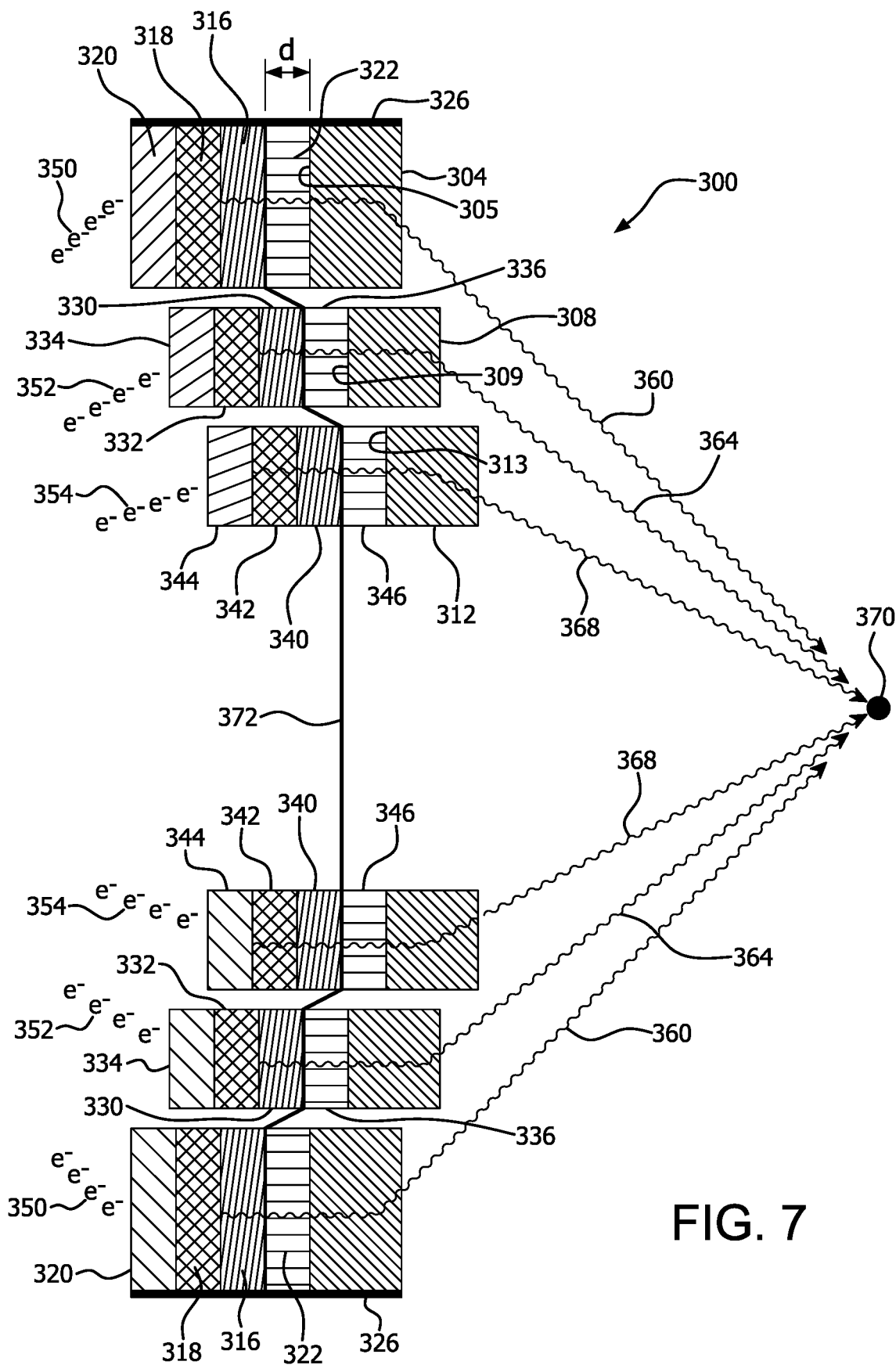
FIG. 7 is a schematic cross-section of an alternative target and focusing lens.

There is shown in FIG. 7 embodiment 300 of a radiation therapy device in which a single target positioned at the outermost ring of a focusing lens assembly is replaced by multiple targets associated with each ring of the focusing lens assembly. In the embodiment shown, the focusing lens is comprised of circular outermost focusing lens ring element 304 with inlet surface 305, middle focusing lens ring element 308 with inlet surface 309, and innermost focusing lens ring element 312 with inlet surface 313. A target 316, substrate layer 318, target-aligning septa 320, and lens-coupled septa 322, as previously described, are associated with the outermost focusing lens ring element 304. A target 330, substrate layer 332, target-aligning septa 334, and lens-coupled septa 336, as previously described, are associated with the middle focusing lens ring element 308. A target 340, substrate layer 342, target-aligning septa 344, and lens-coupled septa 346, as previously described, are associated with the innermost focusing lens ring element 312. More or fewer focusing lens ring elements can be provided, with associated targets.

Associating a target with each focusing lens ring element permits variability in the delivery of x-ray photons to a desired focal point. A steered electron beam 350 can be directed to the target 316. A steered electron beam 352 can be steered to the target 330. A steered electron beam 354 can be directed to the target 340. Control of the electron beam to specific ones of the targets 316, 330 and 340 permits the selected emission of associated x-ray photon beams 360, 364 and 368 directed to the focal spot 370. This variability provides different angles of lines of interaction of the x-ray photons generate an array of converging beams, which in and of themselves do not deposit high dose on their path, yet generate an intense dose deposition at the treatment focal spot 370. This control of beam direction can also be useful for avoiding dose deposition in organs at risk and/or healthy cells that do not require ionization. In this embodiment the vacuum chamber wall 372 is modified to seal each of the targets 316, 330 and 340 within the vacuum chamber. Structure shown schematically as connection 326 mechanically connects the target to the focusing lens.

Figure 8:
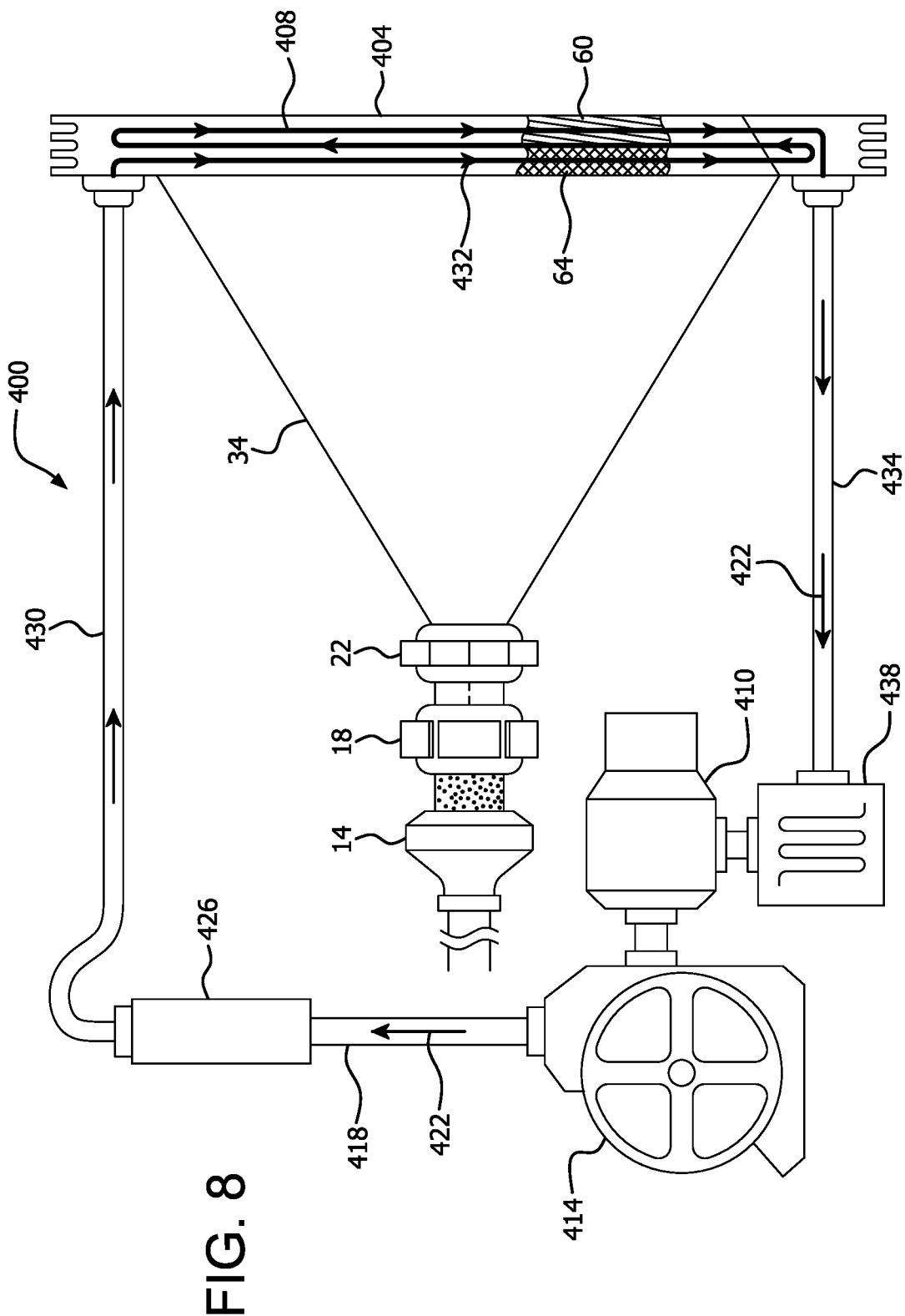
FIG. 8 is a schematic depiction of a cooling circuit for a target.

As shown in FIG. 8 a chilling module 400 is provided for cooling the target 60 and substrate layer 64. A cooling ring 404 can be constructed so as to wrap around the outer circumference of the circular target 60 and substrate layer 64. Internal flow channels 408 are provided and can have a circuitous path through the cooling jacket 404 so as to increase heat exchange of a cooling fluid flowing through the flow channels 408 with the target 60 and substrate layer 64. Although a circular cooling jacket 404 is depicted, various geometries are possible and the cooling jacket 404 can be differently positioned, shaped and sized. The cooling fluid can be selected from a number of possible fluids, including distilled water, oils, some gases, gels, or dedicated refrigerant compounds.

A chiller 410 is provided for actively cooling the cooling fluid. A pump 414 can be provided for recirculation of the cooling fluid. The cooling fluid can travel through a conduit 418 as indicated by arrow 422. A coolant filter 426 can optionally be provided. The coolant fluid travels through a connection 430 to the flow channels 408 of the cooling ring 404. The cooling fluid travels through the flow channels 408 as indicated by arrows 432. A fluid connection 434 returns the cooling fluid to a heat exchanger 438 and to the active chiller 410.

Figure 9:
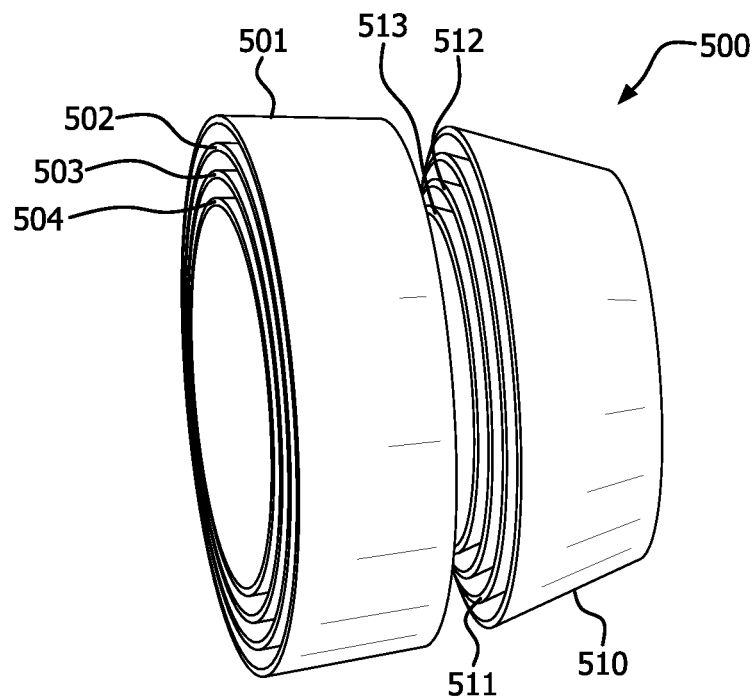
FIG. 9 is a perspective view of a spectral x-ray focusing lens.
Figure 10:
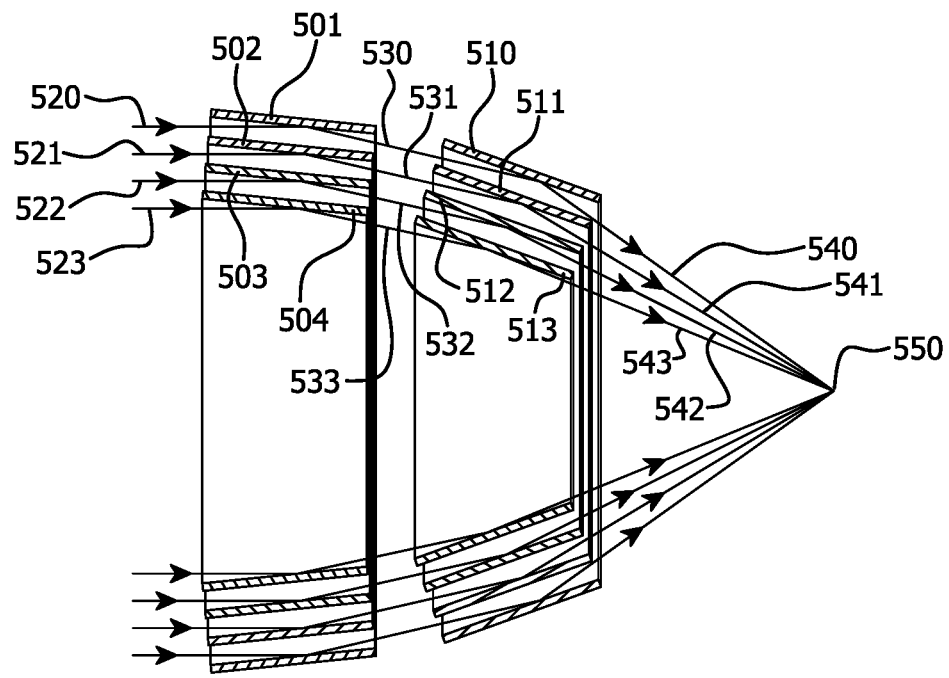
FIG. 10 is a schematic cross section of a spectral x-ray focusing lens.

The invention can be used with many different x-ray focusing lens designs. There is shown in FIGS. 9-10 a spectral x-ray focusing lens 500 which includes a first nested array of cylindrical mirrors 501-504 and a second nested array of cylindrical mirrors 510-513. Incoming x-ray photon beams 520-523 strike inside mirrored surfaces of the cylindrical mirrors 501-504 and are reflected into reflected x-ray photon beams 530-533. The reflected x-ray photon beams 530-533 then strike the second nested array of cylindrical mirrors 510-513 and are reflected into focused x-ray photon beams 540-543 and are directed to a treatment focal point 550.

Figure 11:
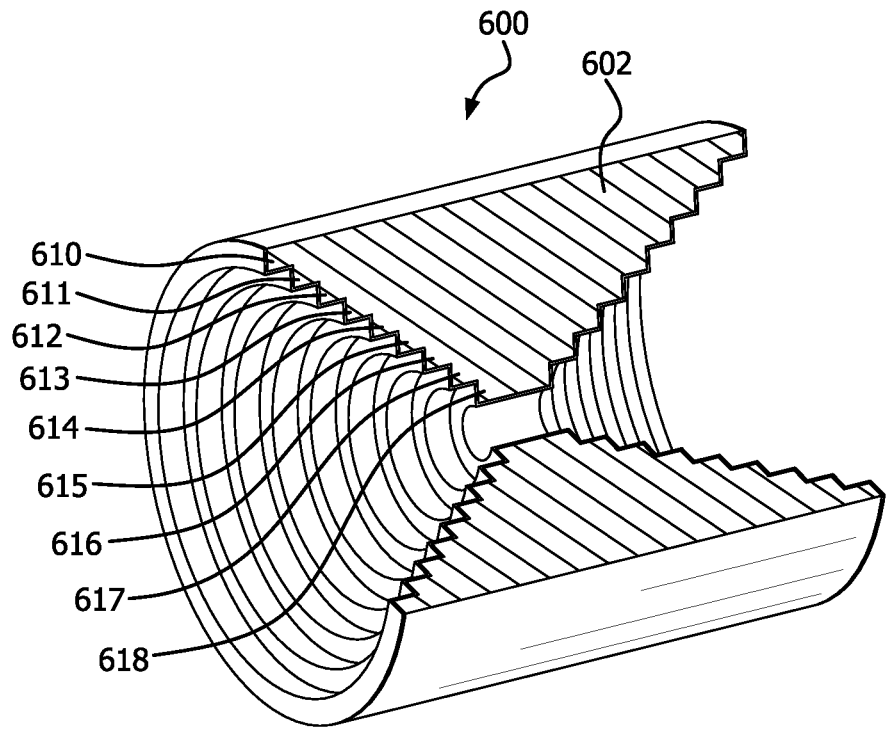
FIG. 11 is a perspective view, partially broken away, of a rolled x-ray prism lens.
Figure 12:
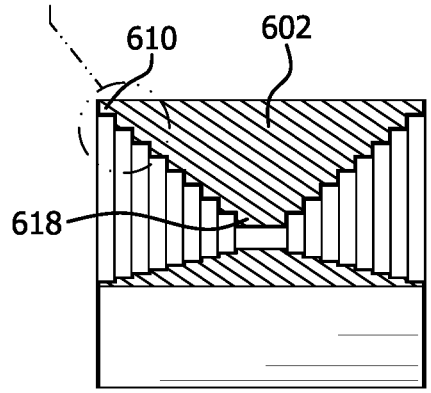
FIG. 12 is a side elevation, partially broken away.
Figure 12A:
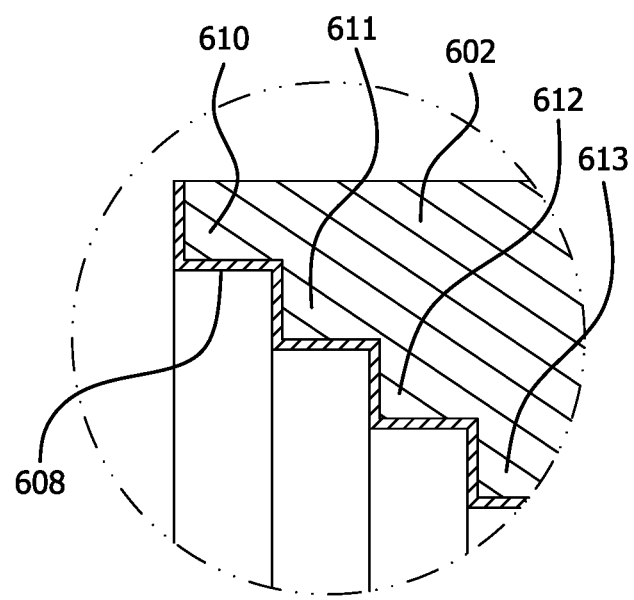
FIG. 12A is an expanded view of area 12A in FIG. 12.

There is shown in FIGS. 11-12 a rolled x-ray prism lens 600 having a generally cylindrical body 602 with a plurality of stepped edges 610-618. The stepped edges 610-618 are covered in a material such as a polyamide film 608 (FIG. 12 and FIG. 12A). The film covered stepped edges are such that x-ray beams near the center encounter just a few such surfaces to deflect the beam slightly, while x-rays passing far from the optical axis are deflected stronger by a larger number of such surfaces.

Figure 13:
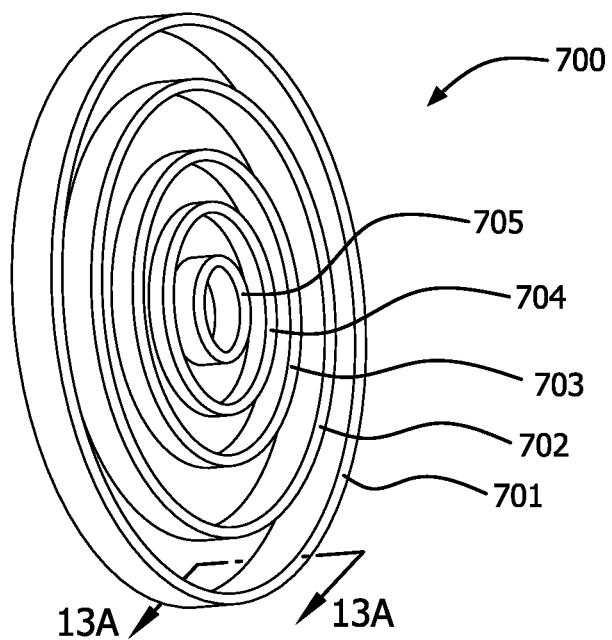
FIG. 13 is a perspective view of a Rowland lens.
Figure 13A:
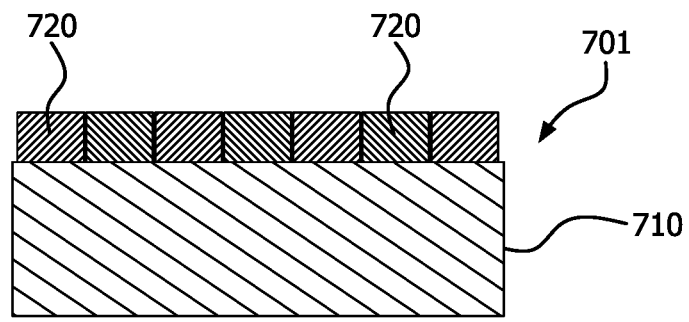
FIG. 13A is a cross section taken along line 13A-13A in FIG. 13.

There is shown in FIG. 13 and FIG. 13A a Rowland lens 700 having a plurality of concentric focusing ring elements 701-705. Surfaces of body 710 the focusing ring elements 701-705 are covered with refracting crystals 720. The x-ray beam striking the outermost focusing ring element 701 are refracted to a greater degree than x-rays striking the focusing ring 702 which is greater than the refraction provided by smaller diameter concentric rings 703, 704 and then 705. The result is that x-ray beams striking the concentric focusing ring elements 701-705 are focused to different degrees, and to a common converging focal point.

Figure 14:
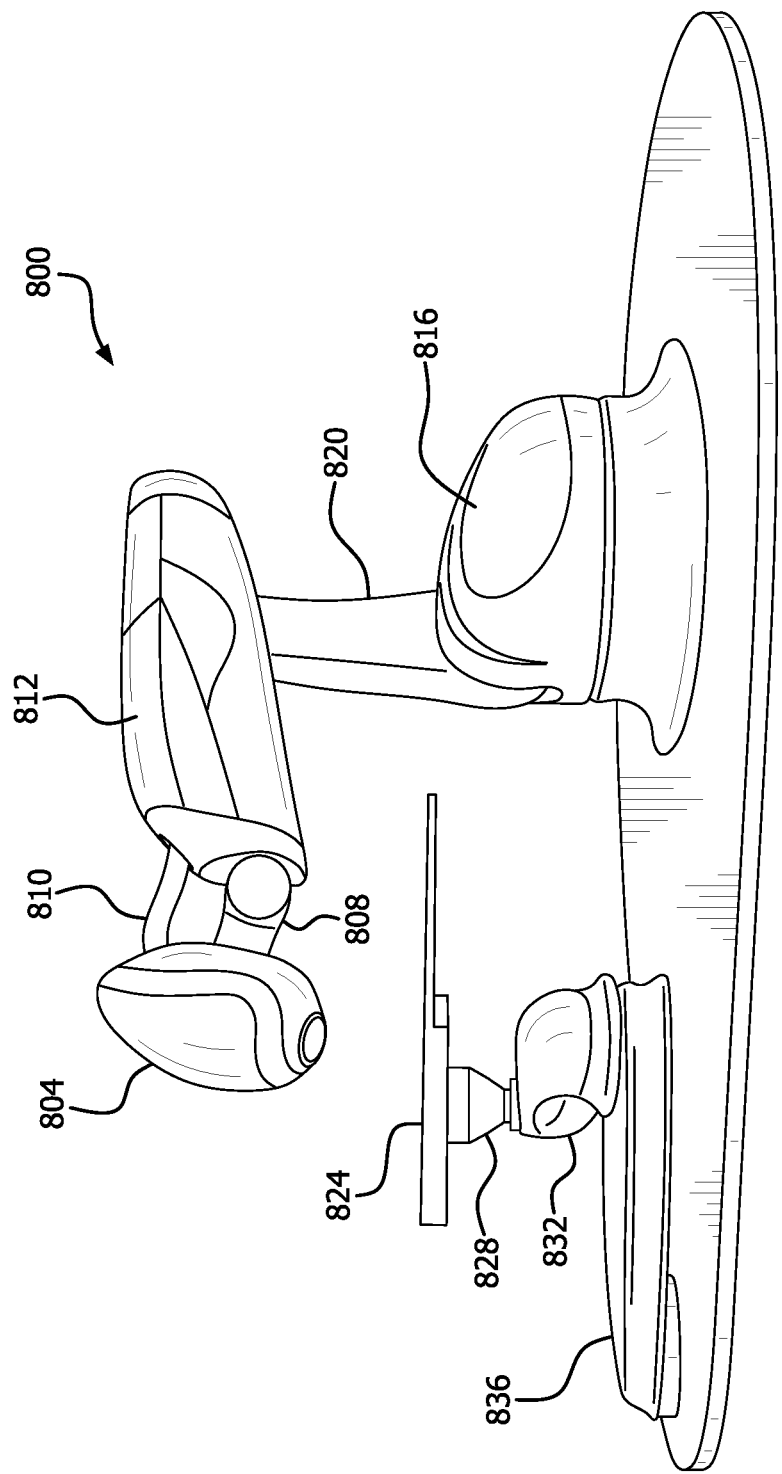
FIG. 14 is a perspective view of a radiotherapy installation preparing to the invention.

There is shown in FIG. 14 a radiation therapy insulation 800 in which a treatment head 804 contains the radiation therapy device of the invention. The treatment head 804 is suspended on a robotic arm 808 and receives power and transmits communication through power and communications trunk 810. A housing 812 contains the remaining portions of the robotic arm, sensors, switches, and control and communications connections. The treatment head 804 and housing 812 are supported on the base 816 by a rotatable supporting arm 820. The patient rests on a support couch 824 supported by a movable axis 828 on a pivoting robotic arm/gimbal 832 on the base 836.

Figure 15:
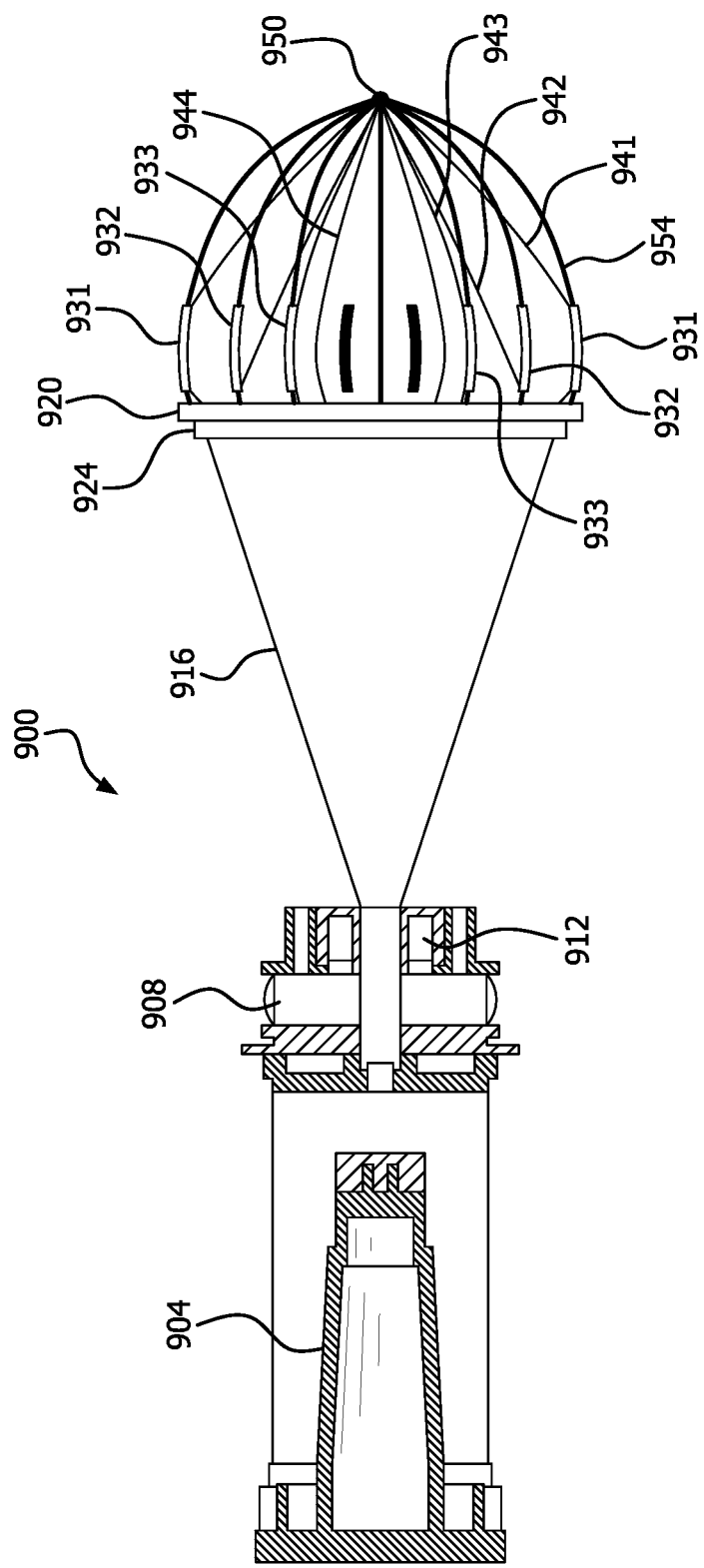
FIG. 15 is a schematic diagram of a radiation therapy device according to the invention.

There is shown in FIG. 15 a radiation therapy device 900 according to the invention which would be mounted within the treatment head 804. The radiation therapy device 900 includes an electron beam source 904, a beam focusing device 908, and a beam steering device 912. The electron beam travels through the vacuum chamber 916 and strikes the target 920 on the support layer 924. X-ray photons generated at the target 920 strike Rowland lens rings 931-933 and generate converging x-ray beams 941-944. These converging x-ray beams converge at focal point 950. A supporting framework 954 can be provided for the Rowland lens.

Figure 16:
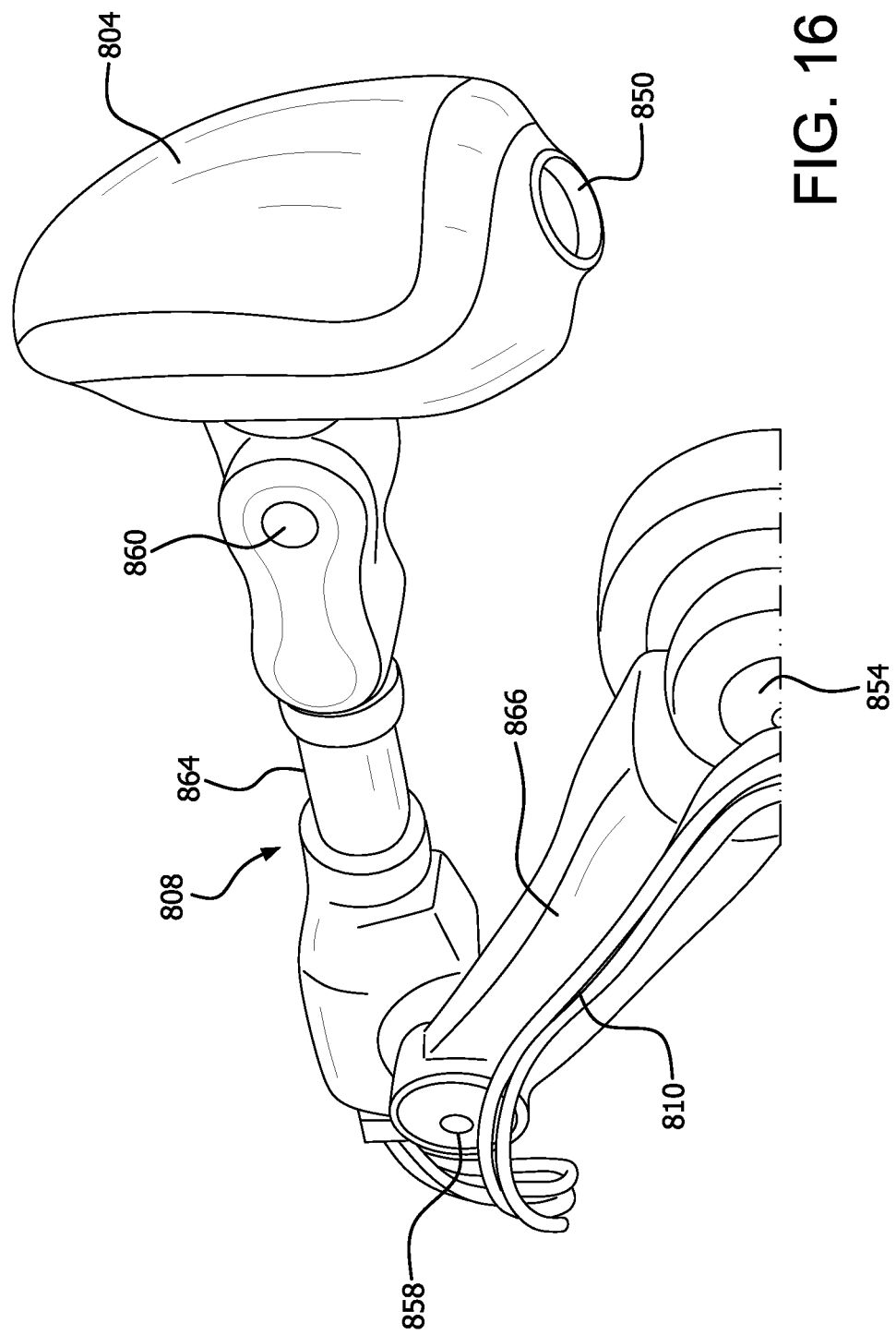
FIG. 16 is a perspective view of a radiation therapy device within a treatment head supported by a robotic arm.

There is shown in FIG. 16 the treatment head 804 with the housing 812 removed to reveal internal features of the supporting robotic arm 808. The treatment head 804 has a beam port 850 for passage of the x-ray photons to the patient. The robotic arm 808 includes first arm segment 864 and second arm segment 866. The treatment head 804 is mounted to the first arm segment 864 by a pivotal mounting axis 860. The first arm segment 864 is connected to the second arm segment 866 by pivotal mounting axis 858. The second arm segment 866 is connected to the supporting arm 820 by pivotal mounting axis 854. Communications, control, and power lines 810 extend from the base 816 to the treatment head 804.

Figure 17:
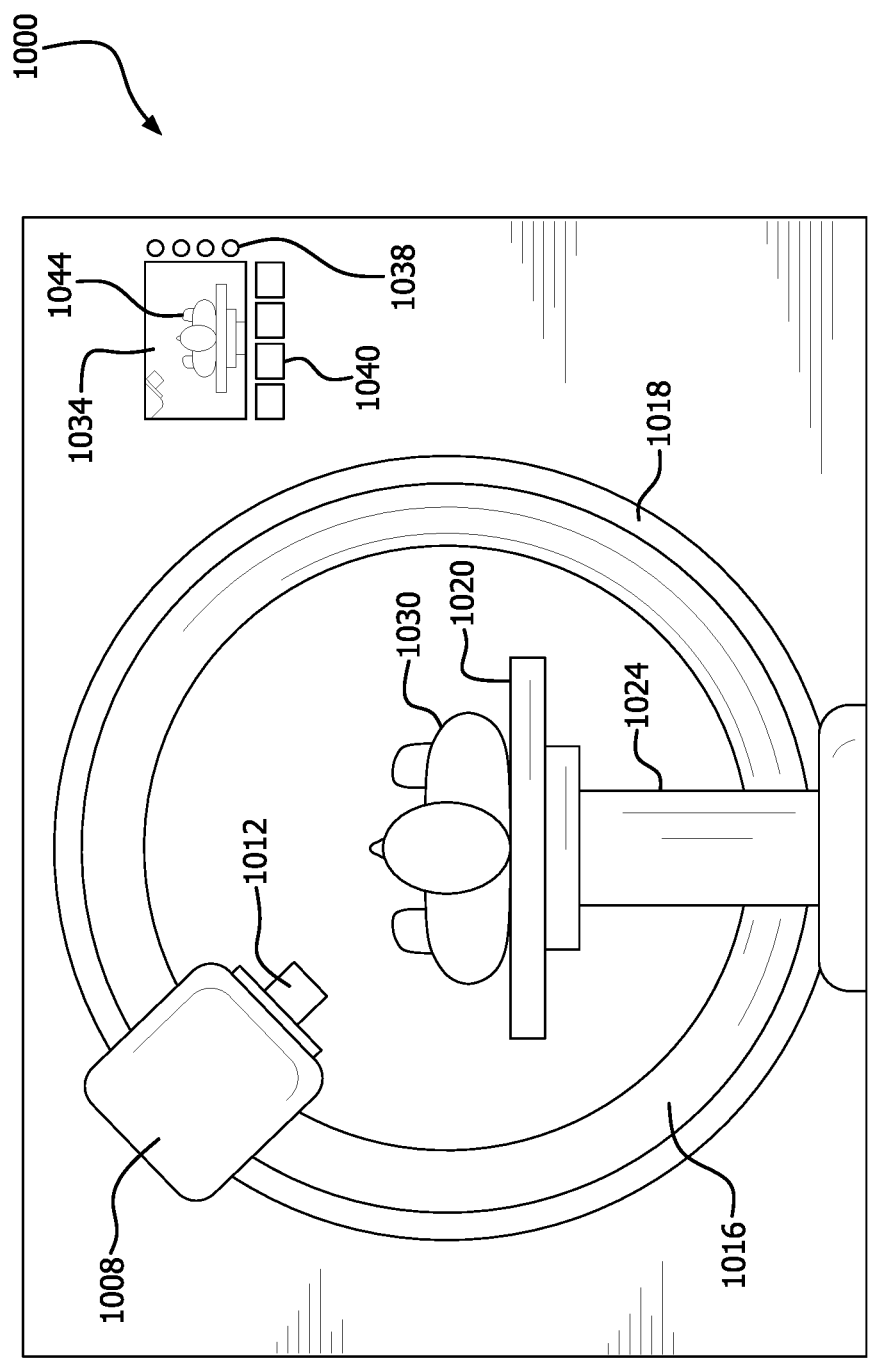
FIG. 17 is a schematic front elevation of a radiation therapy device according to the invention as mounted on a rotating robotic gantry.

There is shown in FIG. 17 an embodiment 1000 of a radiation therapy device in which a treatment head 1008 is mounted to a rotating powered gantry 1016 mounted to a support gantry ring 1018. The patient 1030 rests on a supporting couch 1020 mounted on pedestal 1024. Radiation is administered through x-ray photon port 1012. Control is affected by a control panel 1034 which can include a visual representation of the patient 1044 and various machine and system states. Control panel includes suitable readout and control elements, such as buttons 1038 and touch panel 1040.

Figure 18:
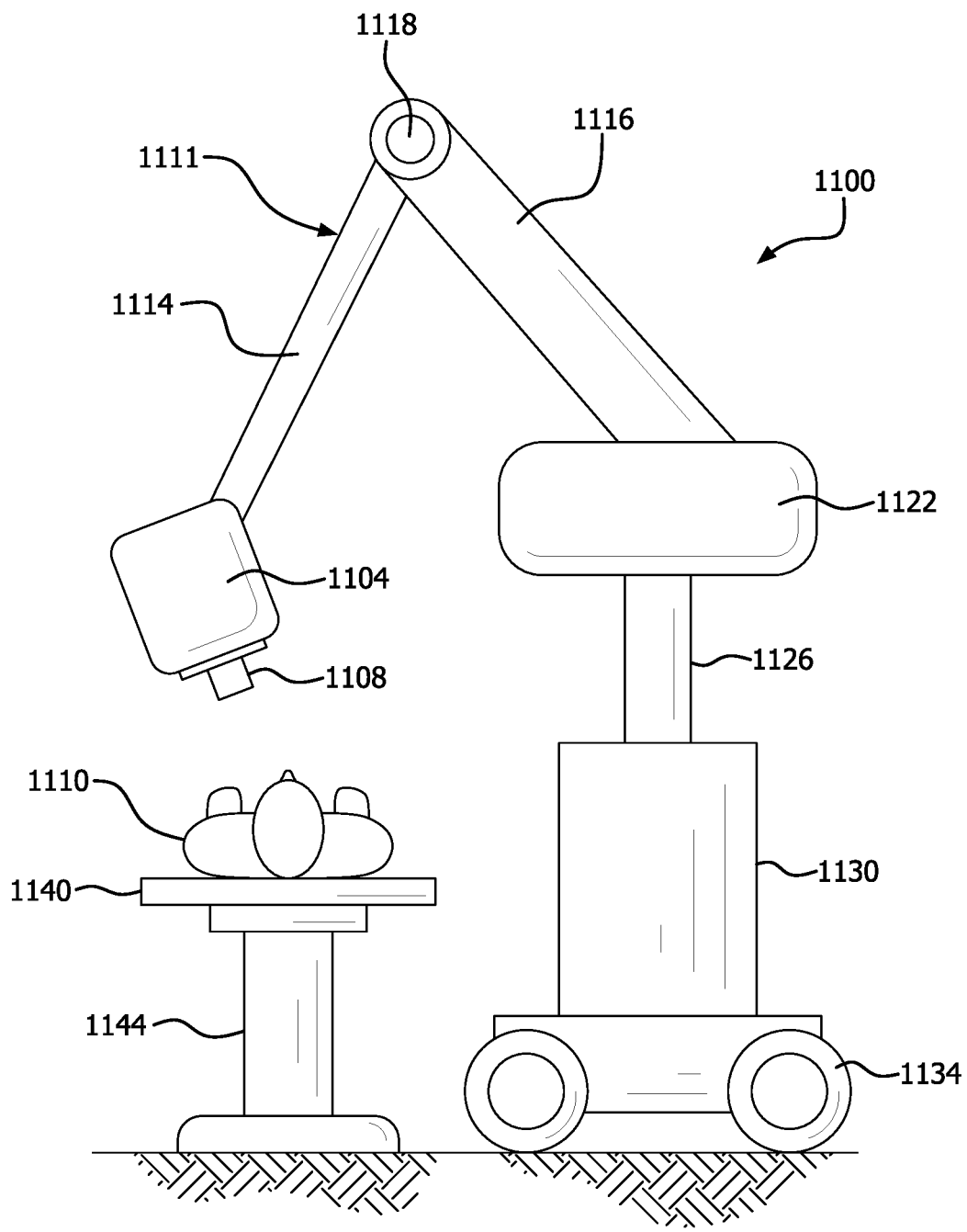
FIG. 18 is a schematic front elevation of a radiation therapy device according to the invention mounted on a manual gantry.

There is shown in FIG. 18 and embodiment 1100 of a radiation therapy device in which a treatment head 1104 is mounted on a manually controlled arm 1111. The treatment head 1104 includes a beam port 1108 for administration of the x-ray photons to the patient 1110. The manual arm 1111 includes a first arm segment 1114 and a second arm segment 1116 connected by pivotal connection 1118. The second arm segment 1116 is connected to the control modules housing 1122 mounted to a pedestal 1126 that is connected to a base 1130. The base 1130 includes the cooling and power modules for the treatment head 1104 and it can be supported on wheels 1134 for mobility. The patient 1110 resides on a patient support couch 1140 which can be mounted on a pedestal 1144.

The invention as shown in the drawings and described in detail herein disclose arrangements of elements of particular construction and configuration for illustrating preferred embodiments of structure and method of operation of the present invention. It is to be understood however, that elements of different construction and configuration and other arrangements thereof, other than those illustrated and described may be employed in accordance with the spirit of the invention, and such changes, alternations and modifications as would occur to those skilled in the art are considered to be within the scope of this invention as broadly defined in the appended claims. In addition, it is to be understood that the phraseology and terminology employed herein are for the purpose of description and should not be regarded as limiting.

I claim:

1. A radiation therapy device, comprising:
   an electron beam source (EBS) for generating an electron beam;
   a steering device for directing the electron beam;
   wherein the electron beam source and the steering device generate a scanning electron beam, and wherein the steering device comprises a deflecting electromagnet for scanning the electron beam;
   a target disposed a predetermined distance from the EBS and positioned to intercept the electron beam, the target element generating x-ray photons upon the impact of electrons with the target;
   a focusing lens coupled to and spaced from the target by no more than 10 mm, and positioned to receive x-ray photons generated by the target, the focusing lens focusing the x-ray photons to a focal point.

2. The radiation therapy device of claim 1, wherein the focusing lens has an inlet geometry and the target is shaped to match the inlet geometry of the focusing lens.

3. The radiation therapy device of claim 1, wherein the attenuation of the x-ray photons from the target to the lens is less than 15%.

4. The radiation therapy device of claim 1, wherein the target comprises a material which produces Bremsstrahlung x-rays when impacted by electrons generated by the electron beam source.

5. The radiation therapy device of claim 1, wherein the target comprises at least one selected from the group consisting of molybdenum, gold, tungsten, rhodium, and brass.

6. The radiation therapy device of claim 1, wherein the focusing lens comprises at least one selected from the group consisting of mirrors, crystals, and polyimide film over a substrate.

7. The radiation therapy device of claim 1, wherein the electron beam source comprises a focusing device for focusing electrons in a pattern.

8. The radiation therapy device of claim 7, wherein the pattern comprises at least one selected from the group consisting of a pencil beam, a cone beam, and an O-shaped beam.

9. The radiation therapy device of claim 1, further comprising a cooling circuit for facilitating the transfer of thermal energy away from the target.

10. The radiation therapy device of claim 1, further comprising an EBS control system that is configured to selectively control the location where the electron beam intersects the target.

11. The radiation therapy device of claim 10, wherein the EBS control system is further configured to selectively control an x-ray dose by selectively varying at least one of an EBS voltage and an electron beam dwell time which are applied when the electron beam intersects the target.

12. The radiation therapy device of claim 1, further comprising a vacuum chamber disposed between the EBS and the target, the EBS configured to cause the electron beam to travel through an enclosed elongated length of the vacuum chamber maintained at a vacuum pressure.

13. The radiation therapy device of claim 1, wherein the target is provided on a substrate layer.

14. The radiation therapy device of claim 13, wherein the substrate layer comprises at least one material selected from the group consisting of diamond, beryllium, aluminum, sapphire, and ceramic.

15. The radiation therapy device of claim 1, wherein the focusing lens comprises concentric lens elements.

16. The radiation therapy device of claim 15, wherein concentric focusing lens elements decrease in diameter in direction extending away from the EBS.

17. The radiation therapy device of claim 1, wherein the focusing lens comprises at least one selected from the group consisting of a Rowland lens, a spectral x-ray focusing lens, and a rolled x-ray prism lens.

18. The radiation therapy device of claim 1, further comprising target-aligning septa comprising a high Z material.

19. The radiation therapy device of claim 18, wherein the high Z material comprises at least one selected from the group consisting of stainless steel, molybdenum (Mo), tungsten (W), and tantalum (Ta).

20. The radiation therapy device of claim 1, further comprising lens-coupled septa comprising a high-Z material, the lens-coupled septa being positioned between the target and the focusing lens.

21. The radiation therapy device of claim 1, further comprising a tomography target for generating tomography multiplane cone beam x-ray photon beams.

22. The radiation therapy device of claim 21, further comprising an x-ray photon detector for detecting the tomography multiplane cone beam x-ray photon beams.

23. The radiation therapy device of claim 22, wherein the detector is movable from a first registered position to a second registered position.

24. The radiation therapy device of claim 21, wherein the tomography target is positioned in the center axis of concentric focusing lens elements.

25. The radiation therapy device of claim 21, comprising a plurality of tomography targets mounted on a concave substrate.

26. The radiation therapy device of claim 25, wherein the concave substrate is parabolic.

27. The radiation therapy device of claim 1, wherein the radiation therapy device is mounted on a positioning device.

28. The radiation therapy device of claim 27, wherein the positioning device comprises at least one selected from the group consisting of a rotating powered gantry, a robotic gantry, and a manual controlled arm.

29. A method for conducting radiation therapy, comprising the steps of:
providing an electron beam source (EBS) for generating an electron beam, a steering device for directing the electron beam, a target disposed a predetermined distance from the EBS and positioned to intercept the electron beam, the target generating x-ray photons upon the impact of electrons with the target, and a focusing lens coupled to and spaced from the target by no more than 10 mm and positioned to receive x-ray photons generated by the target;
generating an electron beam with the EBS and using the steering device to direct the electron beam to the target, wherein the target will generate x-ray photons that will impact the focusing lens;
focusing the x-ray photons with the focusing lens to a focal point; and,
wherein the focusing lens has an inlet geometry and the target is shaped to match the inlet geometry of the focusing lens.

30. A method for conducting radiation therapy, comprising the steps of:
providing an electron beam source (EBS) for generating an electron beam, a steering device for directing the electron beam, a target disposed a predetermined distance from the EBS and positioned to intercept the electron beam, the target generating x-ray photons upon the impact of electrons with the target, and a focusing lens coupled to and spaced from the target by no more than 10 mm and positioned to receive x-ray photons generated by the target;
generating an electron beam with the EBS and using the steering device to direct the electron beam to the target, wherein the target will generate x-ray photons that will impact the focusing lens;
focusing the x-ray photons with the focusing lens to a focal point; and,
wherein the focusing of the x-ray photons is performed by at least one selected from the group consisting of a Rowland lens, a spectral x-ray focusing lens, and a rolled x-ray prism lens.

31. A method for conducting radiation therapy, comprising the steps of:
providing an electron beam source (EBS) for generating an electron beam, a steering device for directing the electron beam, a target disposed a predetermined distance from the EBS and positioned to intercept the electron beam, the target generating x-ray photons upon the impact of electrons with the target, and a focusing lens coupled to and spaced from the target by no more than 10 mm and positioned to receive x-ray photons generated by the target;

generating an electron beam with the EBS and using the steering device to direct the electron beam to the target, wherein the target will generate x-ray photons that will impact the focusing lens;

focusing the x-ray photons with the focusing lens to a focal point; and, further comprising the step of providing a tomography target and directing the electron beam at the tomography target, and generating tomography multiplane cone beam x-ray photon beams by the impact of the electron beam with the tomography target.

32. The method of claim 31, further comprising the step of providing an x-ray photon detector, using the x-ray photon detector for detecting the tomography multiplane cone beam x-ray photon beams.

33. The method of claim 32, further comprising the step of registering a first position of the x-ray detector, and moving the x-ray detector from the first registered position to a second registered position.

34. A radiation therapy device, comprising:

an electron beam source (EBS) for generating an electron beam;

a steering device for directing the electron beam;

a target disposed a predetermined distance from the EBS and positioned to intercept the electron beam, the target element generating x-ray photons upon the impact of electrons with the target;

a focusing lens coupled to and spaced from the target by no more than 10 mm, and positioned to receive x-ray photons generated by the target, the focusing lens focusing the x-ray photons to a focal point; and, a tomography target for generating tomography multiplane cone beam x-ray photon beams when impacted by the electron beam.

\* \* \* \* \*